United States Patent [19]
Orgain

[11] Patent Number: 5,188,611
[45] Date of Patent: Feb. 23, 1993

[54] SAFETY SHEATH FOR NEEDLES, SHARP INSTRUMENTS AND TOOLS

[76] Inventor: Peter A. Orgain, Alger Brook Rd., So. Strafford, Vt. 05070

[21] Appl. No.: 605,568

[22] Filed: Oct. 30, 1990

Related U.S. Application Data

[63] Continuation-in-part of Ser. No. 530,997, May 31, 1990, abandoned.

[51] Int. Cl.$^5$ .............................................. A61M 5/32
[52] U.S. Cl. ..................................... 604/192; 604/263
[58] Field of Search ................ 604/192, 187, 263, 198

[56] References Cited

U.S. PATENT DOCUMENTS

| | | | |
|---|---|---|---|
| 4,820,277 | 4/1989 | Norelli | 604/192 |
| 4,976,699 | 12/1990 | Gold | 604/192 |

FOREIGN PATENT DOCUMENTS 2620341  3/1989  France ................ 604/198

*Primary Examiner*—John D. Yasko
*Attorney, Agent, or Firm*—Cesari and McKeanna

[57] ABSTRACT

A reusable arrangement to protect against accidental contact with the sharp surfaces of needles and other invasive medical instruments. In one embodiment, the invention comprises a collar that engages a sharp surgical instrument in advance of its sharp end. Attached to the collar by means of a hinge is a slotted longitudinal member, which swings over the sharp end of the instrument, thereby engaging either the collar or the portion of the instrument just in front of the collar and also retaining the instrument behind a keeper shelf. The keeper shelf may be engaged with the opposite side of the longitudinal member to lock this member over the sharp instrument. The longitudinal member may also be equipped with wing members to facilitate movement of the sharp instrument around the keeper shelf. In another embodiment, the locking mechanism comprises a set of flanges depending from the longitudinal member that are gripped by complementary catches on the collar when the device is placed into the closed position.

3 Claims, 18 Drawing Sheets

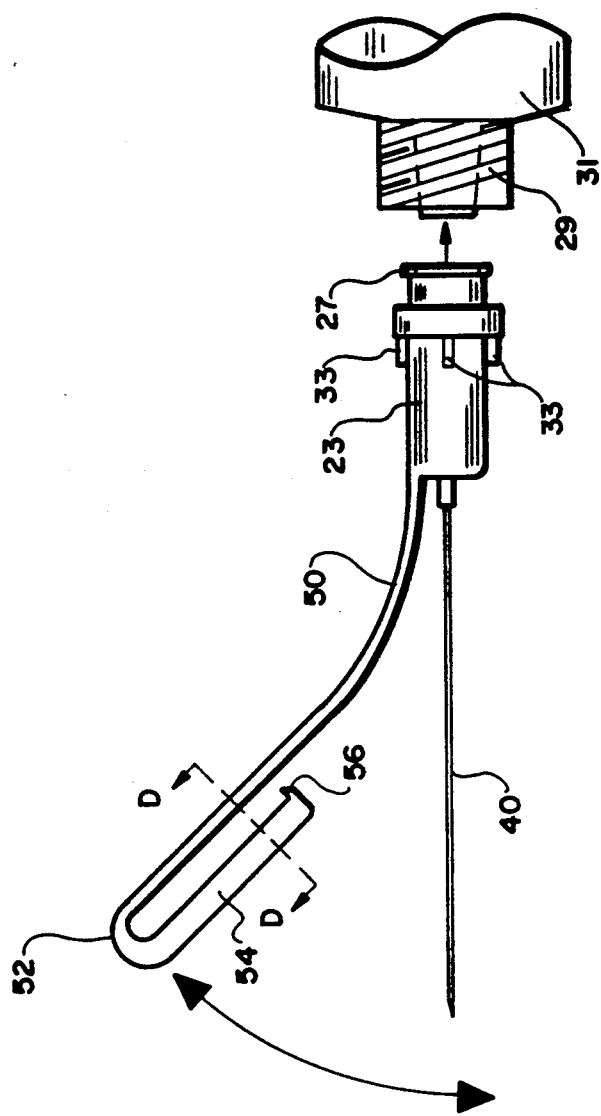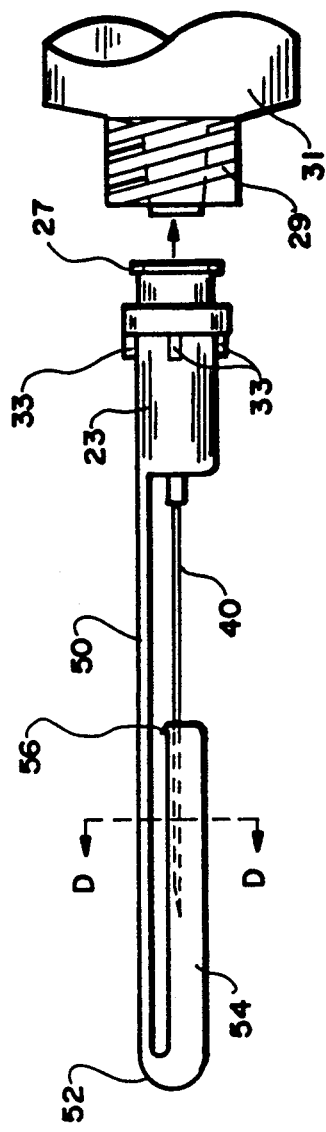
FIG. 9
FIG. 10

SAFETY SHEATH FOR NEEDLES, SHARP INSTRUMENTS AND TOOLS

This is a continuation-in-part of Ser. No. 07/530,997 filed May 31, 1990, now abandoned.

BACKGROUND OF THE INVENTION

1. Field of the Invention

The present invention relates to safe storage for hypodermic and other needles, surgical instruments and sharp tools; more particularly, it relates to a reusable arrangement to protect against accidental contact with the sharp surfaces of needles, invasive medical instruments and other sharp tools.

2. Description of the Related Art

Although accidental wounds due to contact with sharp medical instruments have long plagued health care practitioners, the associated dangers were frequently minimized until the recent spread of the AIDS virus. Over 20 different pathogens are known to have been transmitted by needle-stick injuries. Accordingly, numerous devices have been introduced to minimize or discourage contact between sharp medical devices and their users.

Suitable safety devices must offer favorable structural and operational characteristics. One highly useful structural attribute is compatibility with a range of invasive medical instruments. For example, health care practitioners associate the term "needle" with a variety of devices, including the familiar hypodermic needle, phlebotomy needles, butterfly sets, intravenous catheter stylets, intravenous needle assemblies, prefilled cartridge systems and a variety of other sharp venipuncture instruments. In order to simplify manufacture and encourage industry acceptance, a good design will be usable with a range of related devices.

Other important structural characteristics include low cost of manufacture, a secure locking mode to prevent inadvertent exposure of the sheathed implement, and accurate alignment with the implement to assure reliable operation. The unsheathing operation should be both convenient and resistant to accidental execution (characteristics that tend to oppose one another), while resheathing must be convenient and resistant to mishandling that could cause contact with the instrument. In the specific case of needles, manufacturing difficulties are eased if the sheathing component can be produced with the needle as a unitary construction (e.g., as an extension of the needle hub).

Advantageous operational features include simple and intuitive use, accommodation of frequent sheathings and unsheathings, and the propensity not to interfere—either mechanically or visually—with the operator's use of the unsheathed implement. In the specific case of needles, the user's hands should remain behind the needle during sheathing; it is also useful to provide for fluid discharge after the needle is resheathed.

The prior art includes a large number of needle packaging structures. For example, U.S. Pat. No. 4,867,746 describes a needle shield that exhibits a number of the disadvantages associated with the prior art. The user of this device places the blunt front-end hood against a patient's skin, and proceeds to apply force to drive the needle into the skin at a point anterior to the hood (as shown in FIGS. 4 and 5 of the patent). During this operation, the user is prevented from viewing both the progress of the needle and its entry point. Such observations are important both to maintain precise control over the location of the entry point (which can be critical) and to minimize patient discomfort through choice of the angle of entry. Furthermore, the '746 shield appears to be useful only for needle insertions that are performed at a low angle, since this device relies on the patient's skin to serve as a platform for movement of the shield away from the needle. These limitations render this device particularly unsuitable for use with a large number of surgical instruments (such as scalpels), where the user's line of sight and mechanical freedom cannot be impaired.

U.S. Pat. No. 4,664,259 exemplifies another type of prior-art device that relies on a hinge, rather than flexion, to control withdrawal of the container and consequent exposure of the needle. This device appears to have been designed for one-time needle use (which may or may not be the case in a given clinical context) and during operation may exert force on the needle that could result in its breakage. Like the '746 shield, this device contains no mechanism for assuring non-interference with the user's observation or handling of the needle. The '259 patent does not suggest integral construction with the needle hub.

U.S. Pat. No. 3,658,061 appears to disclose a needle guard comprising an elongated flexible plastic sleeve member with a longitudinal slot adapted to frictionally snap over the entire length of the needle. With this design, the efficacy of the locking mechanism appears to depend on the force exerted on the needle by the edges of the longitudinal sleeve; consequently, achieving a reliable lock might require force that can damage the needle. This design also appears unsuitable for adaptation to surgical instruments other than needles, since its locking mechanism depends on a characteristic curved shape.

All of these devices provide for a single locking mode and appear to contemplate one-handed operation. Few appear to provide for convenient ejection of fluid through the needle when the device is in the closed position.

DESCRIPTION OF THE INVENTION

Objects of the Invention

Accordingly, it is an object of the present invention to provide a sheathing construction that does not interfere with operation of the unsheathed medical device and that can be manufactured integrally with such a device.

It is a further object of the invention to provide a design that can be used with a variety of surgical instruments and sharp tools.

It is another object of the invention to provide a sheathing construction for surgical instruments that encourages the user to unsheath the instrument with two hands, while facilitating closure with one finger behind the instrument's sharp edge or tip.

Yet another object of the present invention is to provide a sheathing construction that features two locking modes, neither of which presents significant stress to the sheathed instrument.

It is a further object of the invention to provide a sheathing construction that can be used repeatedly.

It is another object of the invention to provide a sheathing construction for needles that permits convenient ejection of fluid after the needle has been resheathed.

It is yet a further object of the invention to provide a sheathing construction that aligns itself with the implement to be sheathed.

Another object of the present invention is to provide a sheathing construction that is ambidextrous and intuitively obvious to use.

Other objects will, in part, be obvious and will, in part, appear hereinafter. The invention accordingly comprises an article of manufacture possessing the features and properties exemplified in the constructions described herein and the apparatus embodying the features of construction, all as exemplified in the following summary and detailed description, and the scope of the invention will be indicated in the claims.

Brief Summary of the Invention

All five embodiments of the invention accomplish the foregoing with sets of interrelated mechanical features. In a first embodiment, the invention comprises a collar that engages a sharp surgical instrument in advance of its sharp end. Attached to the collar by means of a flexible hinge is a slotted longitudinal member, which swings over the sharp end of the instrument. The posterior (hinged) portion of the longitudinal member forms a partial sleeve that fits snugly over either the collar or the portion of the instrument just in front of the collar, so as to snap over (or otherwise frictionally engage) the collar or instrument upon application of a slight force by the operator. This furnishes one locking mechanism.

A second locking mechanism is provided by a "keeper shelf", which depends from the longitudinal member and extends through the interior of this member at skew angle. Upon introduction of the implement through the slot into the interior portion of the longitudinal member, the keeper shelf slides the implement laterally, the implement then snapping into a position that obstructs subsequent movement of the implement toward the slot. Alternatively, the keeper shelf can be made thinner to act as a stiff flap that snaps past the needle without bending it as the longitudinal member is closed thereover.

In the case of a sturdy keeper shelf, the user must shift the longitudinal member in a transverse direction in order to remove the sheath, maneuvering the sharp end of the instrument around the keeper shelf. This will generally require a two-handed manipulation. By contrast, the sheath can be fitted over the instrument by swinging the longitudinal member with one hand; the snugly fitting partial sleeve and the longitudinal slot serve as guides that promote alignment between the longitudinal member and the sharp end of the instrument.

The preferred fabrication material for the invention is injection-molded plastic. Consequently, where the invention is used to sheath a needle, the longitudinal member can be hinged to the needle hub, and the entire assembly molded as a single unit. The longitudinal member can also be provided with an aperture at the end thereof, which permits convenient ejection of fluid when the needle has been resheathed between or after uses.

In a variation of this embodiment, two wing members are added to the outer portion of the sheath to allow the user to laterally distort the sheath body, thereby widening the gap between the side wall and the keeper shelf. This facilitates easier removal of the sheath while retaining the safety of two-handed operation.

A further varation of this embodiment includes protuberances along the inner surface of the sheath that engage complementary detents on the needle hub. When the sheath is open, this feature prevents it from freely moving toward the closed position; when the sheath is closed, this feature provides an additional locking mechanism.

In the second embodiment, the collar extends into an arcuate sheath, which is molded to assume a rest position that bends away from the sharp end of the instrument (and out of the user's line of sight). This arcuate sheath ultimately forms an elbow curl and extends back toward the collar, thereby forming upper and lower arcuate portions. The lower portion terminates in a set of flanges that help define a trough to carry the sharp end of the instrument. The user sheaths the instrument by flexing the elbow-tip of the bent upper arcuate portion toward and to either side of the instrument until the bottom arcuate portion passes beneath the sharp end; the user then moves the sheath laterally so that the sharp end of the instrument enters the space between the upper and lower arcuate portions. Upon release by the user, the sheath naturally bends upward, thereby urging the sharp end of the instrument against the lower arcuate portion.

The lower arcuate portion contains two flanges that extend outward, thereby forming a trough for holding the sharp end of the instrument. These flanges can be designed to fit within complementary detents in the body of the upper arcuate segment, enabling the user to permanently lock the sheath around the instrument.

In a variation of this embodiment, a stop depends downward from the upper arcuate portion toward the trough. This feature helps guide the needle to rest in the trough.

In a third embodiment, the lower arcuate portion of the second embodiment is replaced with dual arcuate segments that lie adjacent one another to form a trapping arrangement, which captures the sharp end of the instrument with a minimum of applied force but resists subsequent release of the instrument.

In a fourth embodiment, the construction of the first embodiment is modified to permit the sheath to be firmly locked over the needle after use. In this version, the free edge of the keeper shelf is provided with barbs that may be introduced through a window on the opposite side of the sheath; the barbs are shaped to catch the outer surface of the sheath so as to prevent movement of the shelf back through the window. Thus, by pinching the sheath, the user forces the barbed edge of the keeper shelf through the window, thereby effectively locking the sheath in place over the needle.

In a fifth embodiment, the keeper shelf is replaced with (or augmented by) a set of sheath flanges that engage complementary catches, thereby gripping the sheath in the closed position. Preferably, this embodiment is provided with a living hinge and a strap spring to keep the sheath open unless positively closed by the user. This hinge-and-spring arrangement can be used with any of the sheath-type embodiments of the present invention.

BRIEF DESCRIPTION OF THE DRAWINGS

The foregoing discussion will be understood more readily from the following detailed description of the invention, when taken in conjunction with the accompanying drawings, in which:

FIG. 9 is a side view of the second embodiment of the invention, designed to sheath a hypodermic needle, in the open (unsheathed) position;

FIG. 10 is a side view of the embodiment depicted in FIG. 9, in the closed (sheathed) position;

DETAILED DESCRIPTION OF THE INVENTION

Figure 1:
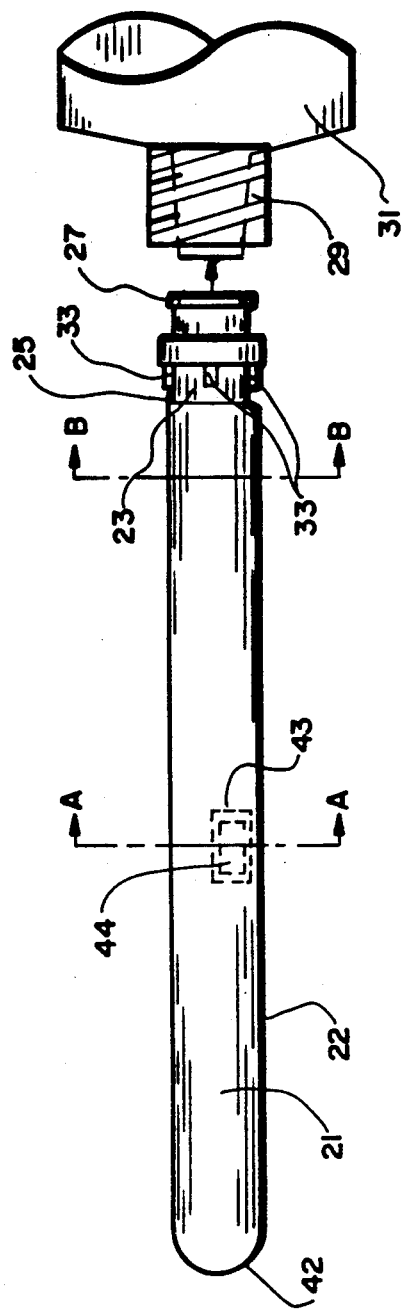
FIG. 1 is a side view of the first embodiment of the invention, designed to sheath a hypodermic needle, phlebotomy needle or intravenous assembly needle.

Refer first to FIG. 1, which shows a side view of the first embodiment of the invention adapted to sheath a hypodermic needle. As heretofore noted, the device may be configured to package a number of different surgical instruments, such as scalpels, as well as picks, awls and other sharp-edged and sharp-pointed instruments. For convenience and consistency of presentation, this description will be confined to designs adapted for needles, it being understood that a variety of other surgical and non-surgical devices can be accommodated by appropriate design changes (which will be readily apparent to one skilled in the art).

As shown in FIG. 1, a longitudinal member 21 covers a needle (not visible in FIG. 1, but denoted by reference numeral 40 in FIG. 2) that extends from a needle hub 23. Longitudinal member 21 is integral with hub 23 and affixed thereto by means of a hinge 25. As stated earlier, the invention is preferably fabricated from injection-molded plastic, which permits one-piece molding of longitudinal member 21 and needle hub 23 (connected by hinge 25). Longitudinal member 21 contains an axial slot 22, which slides over needle 40.

Figure 2:
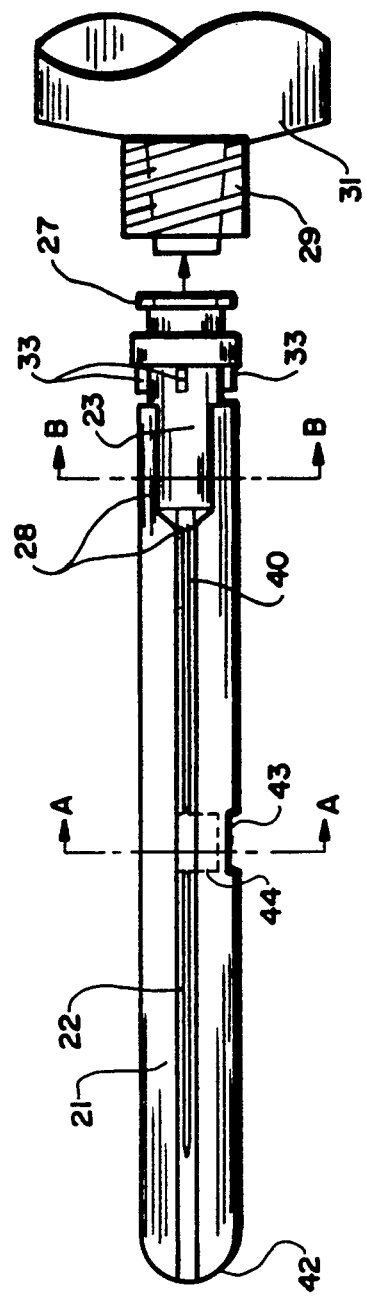
FIG. 2 is a bottom view of the embodiment depicted in FIG. 1, which has been rotated 90 degrees about its axis.
Figure 5:
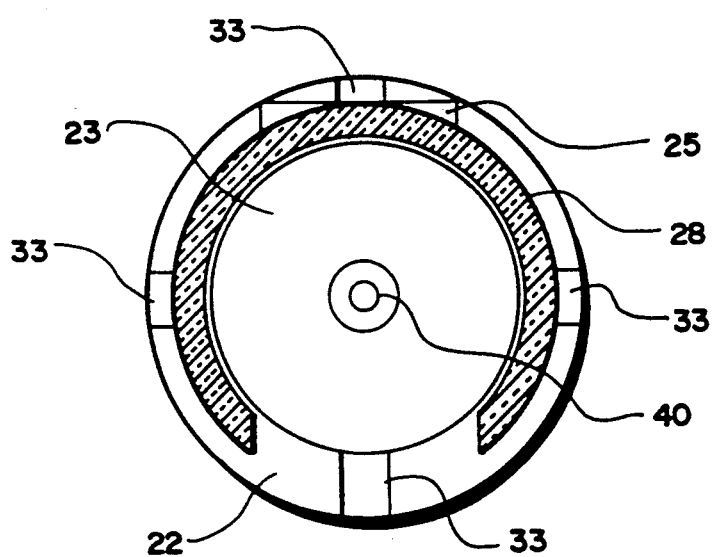
FIG. 5 is a section taken along line B—B of FIG. 1.

The configuration of needle hub 23 is shown with greater particularity in FIG. 2. As shown therein, hub 23 terminates in a set of luer tabs 27, which thread into a standard threaded luer 29 for attachment to a syringe or other receiving device 31. Hub 23 also contains a set of torque vanes 33 mounted on a bearing ring to facilitate convenient threading of luer tabs 27. Slot 22 widens at the point where longitudinal member 21 fits over hub 23, and it thereby forms a partial sleeve 28. Partial sleeve 28 is shaped to fit snugly over hub 23 so as to snap thereon along its length (see FIG. 5); alternatively, the sides of partial sleeve 28 can be substantially parallel, but textured to frictionally engage hub 23 (which can also be textured).

Figure 3:
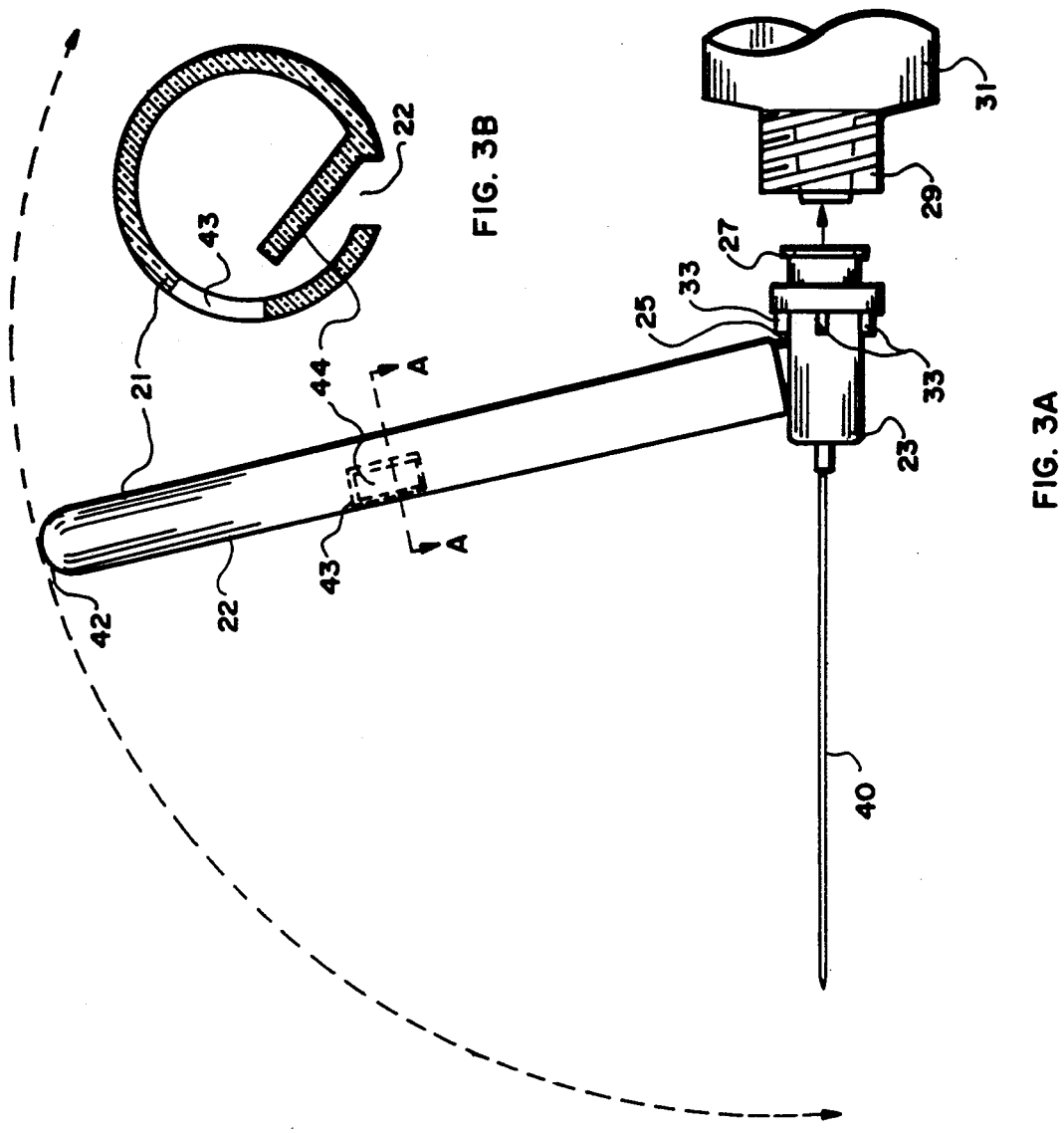
FIG. 3A is a side elevational view of the embodiment depicted in FIG. 1, with the sheath in the raised position.
FIG. 3B is a section taken along line A—A of FIG. 3A.

Operation of the sheath is depicted in FIG. 3A. Upon disengagement of needle 40 from the keeper shelf (which will be described below), the user applies a slight force to tip 42 of longitudinal member 21 along the direction indicated by the upward arc of the arrow, thereby disengaging partial sleeve 28 (and thereby longitudinal member 21) from needle hub 23.

Figure 4:
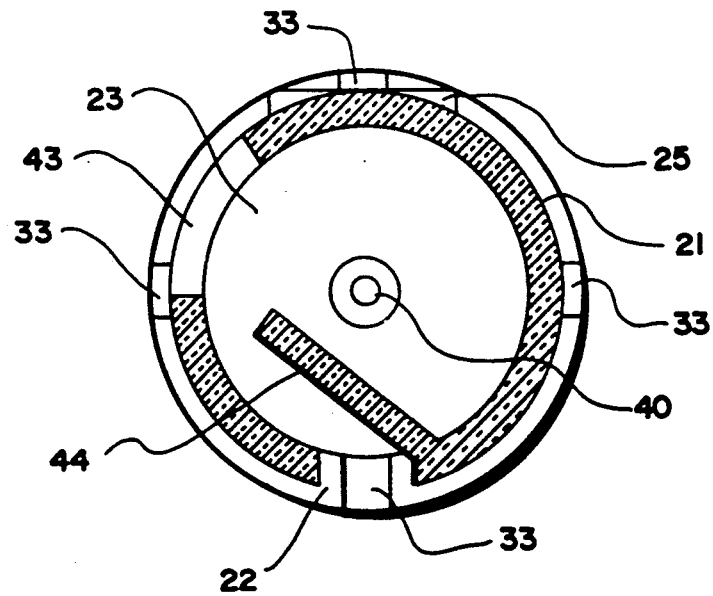
FIG. 4 is a section taken along line A—A of FIG. 1.

Keeper shelf 44, which provides the second locking mechanism of this embodiment of the invention, is shown in FIGS. 3B and 4. Keeper shelf 44 is integral with and depends from longitudinal member 21, extending from the inner wall thereof across (and preferably beyond) slot 22. When the sheath is closed, which is accomplished by exerting a slight force on longitudinal member 21 along the downward arc of the arrow, needle 40 passes through slot 22 and is forced by keeper shelf 44 to the side. After needle 40 has passed the end of keeper shelf 44, needle 40 snaps back into its natural centered position. Alternatively, keeper shelf 44 can be made thinner to act as a stiff flap that snaps past needle 40 (without forcing it to the side) as longitudinal member 21 is closed.

As shown in FIG. 4, after passing keeper shelf 44, needle 40 occupies a position thereabove; keeper shelf 44 then blocks movement of needle 40 back in the direction of slot 22. The operator can verify this status by looking through a keeper window 43, which is described in fuller detail below.

Accordingly, to unsheath needle 40, the user must first manipulate longitudinal member 21 to the right and then upward (from the perspective shown in FIG. 4) to place the needle above slot 22 but below keeper shelf 44. The user then applies a continued upward force to disengage the lower portion of longitudinal member 21 from needle hub 23 (as heretofore described). Note that while unsheathing is generally a two-handed operation, needle 40 may be sheathed with one finger. This is due to the natural alignment provided by partial sleeve 28 and slot 22.

Figure 6:
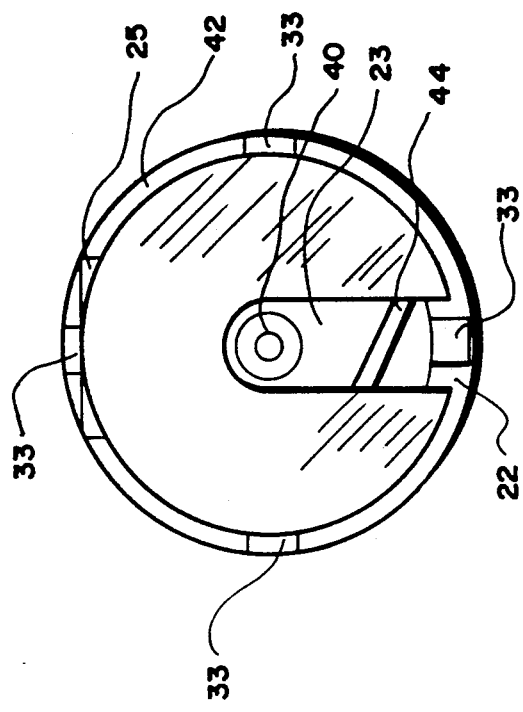
FIG. 6 is an end view of the embodiment depicted in FIG. 1.

As shown in FIG. 6, tip 42 of longitudinal member 21 can contain an aperture or other opening (in FIG. 6, the opening is a sectional cut that continues slot 22 up to tip 42). Keeper shelf 44 may be made visible by a small window 43 (shown most clearly in FIGS. 1 and 4) cut in the side of longitudinal member 21 opposite the position of keeper shelf 44, thereby permitting the operator to readily assess the locked or unlocked status of the needle.

Figure 7:
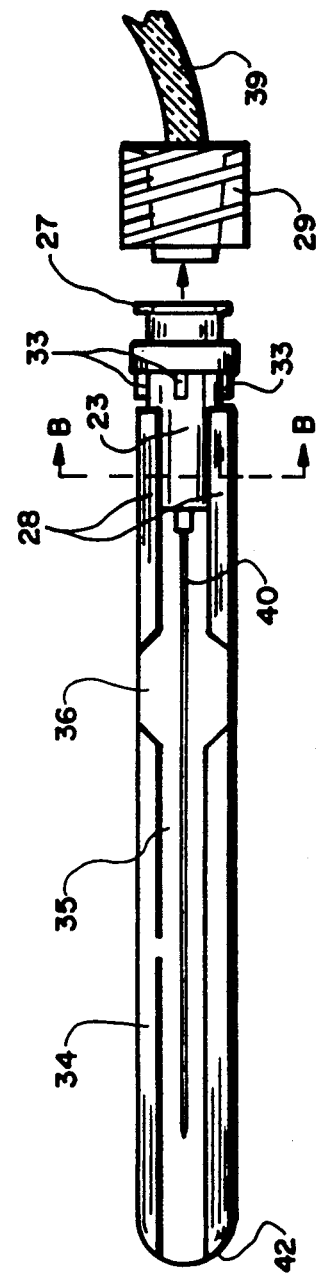
FIG. 7 is a bottom view of a modified version of the first embodiment, which has been adapted for use as an intravenous assembly clamp.
Figure 8:
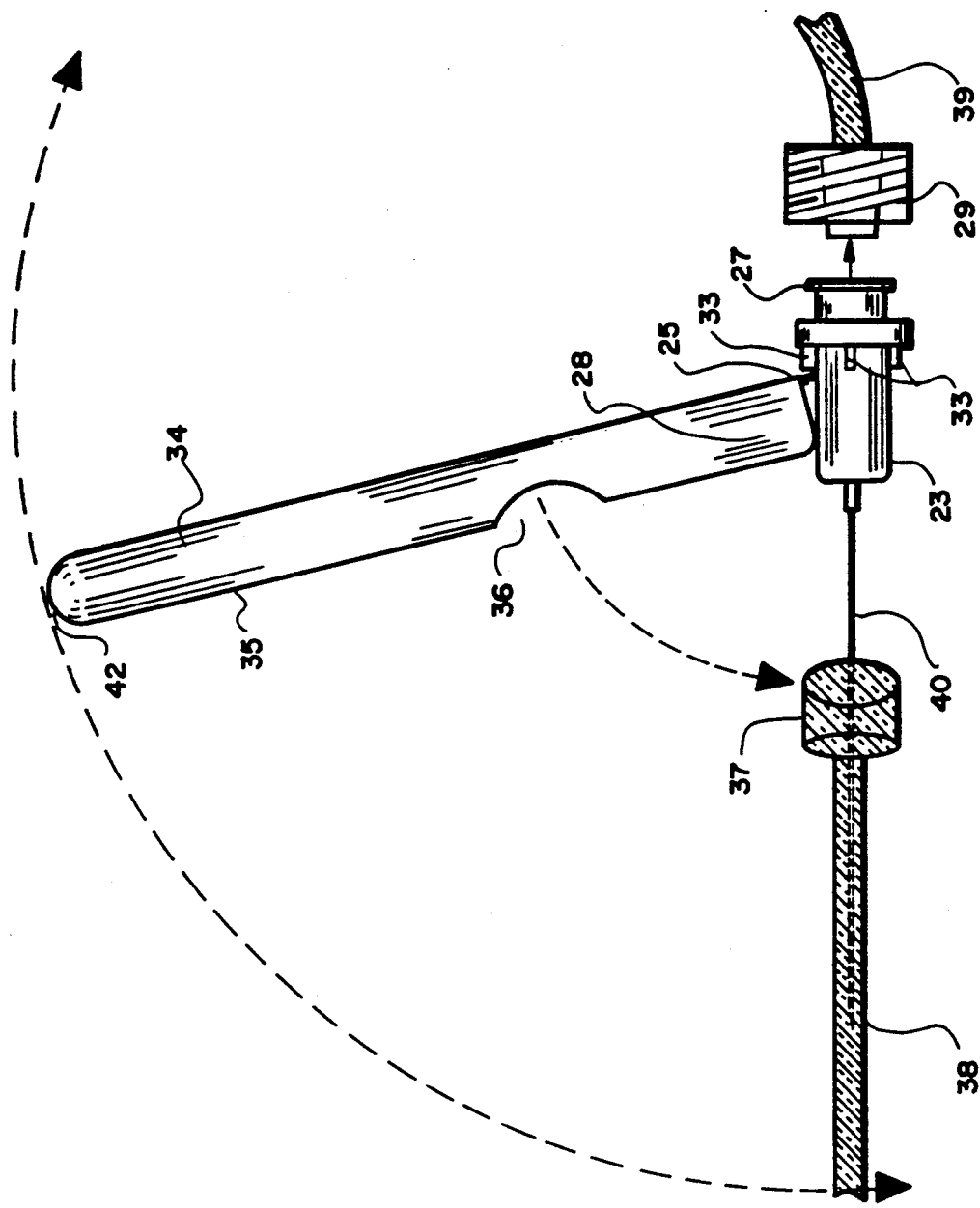
FIG. 8 is a side elevational view of the device depicted in FIG. 7.

This construction of this embodiment can be modified slightly to enable use as both a needle protection sheath and an intravenous assembly clamp. The modified design is depicted in FIGS. 7 and 8. As shown in FIG. 7, longitudinal member 34 is equipped with a wide slot 35 and a cutout 36 toward its proximal end. As in the unmodified version, longitudinal member 34 shields the operator from contact with the needle when it is not in use.

In operation, luer tabs 27 are screwed into a luer lock receiver 29 affixed to an intravenous gravity supply tube 39. The operator then establishes the intravenous assembly connection by piercing a standard rubber diaphragm assembly 37 with needle 40, in the manner conventional for such devices. When longitudinal member 34 is drawn downward along the arc depicted in FIG. 8, an enlarged cavity 36 in longitudinal member 34 encloses diaphragm assembly 37 and wide slot 35 encloses the intravenous delivery tube 38. Clamping action can be provided by the fit of longitudinal member 34 over needle hub 23, the fit of enlarged cavity 36 over diaphragm assembly 37, the fit of wide slot 35 over tube 38, or some combination thereof.

Two further variations on this design are depicted in FIGS. 16-24; although these drawings present the fourth embodiment, the features now described may also be employed in connection with the first embodiment. The first variation involves replacement of hinge 25 with a set of pivot pegs 76 (shown most clearly in FIG. 18) that fit within a set of complementary pivot holes 80, and addition of a set of locking protrusions 78 that engage a complementary set of detents 74a and 74b in needle hub 23. In order to accommodate these features, longitudinal member 21 terminates in a swing arm 82, which fits snugly over the forward portion of hub 23. When longitudinal member 21 is in the closed position, covering needle 40, protuberances 78 rest within detents 74b. In order to move longitudinal member 21 into the open position, sufficient rotative force must be exerted to lift protuberances 78 out of detents 74b. As the swing arm 82 of longitudinal member 21 is rotated about pivot pegs 76, it ultimately reaches a critical angle (preferably 90 degrees) at which protuberances 78 engage detents 78a, thereby securing longitudinal member 21 in the open position. Obviously, it is possible to replace the protuberances on swing arm 82 with detents, and the detents needle hub 23 with complementary protuberances. As depicted most clearly in FIG. 15, in our preferred version detent 74b extends all the way up the front portion of needle hub 23; this simplifies manufacture by allowing swing arm 21 to be installed on either side of needle hub 23.

Figure 23:
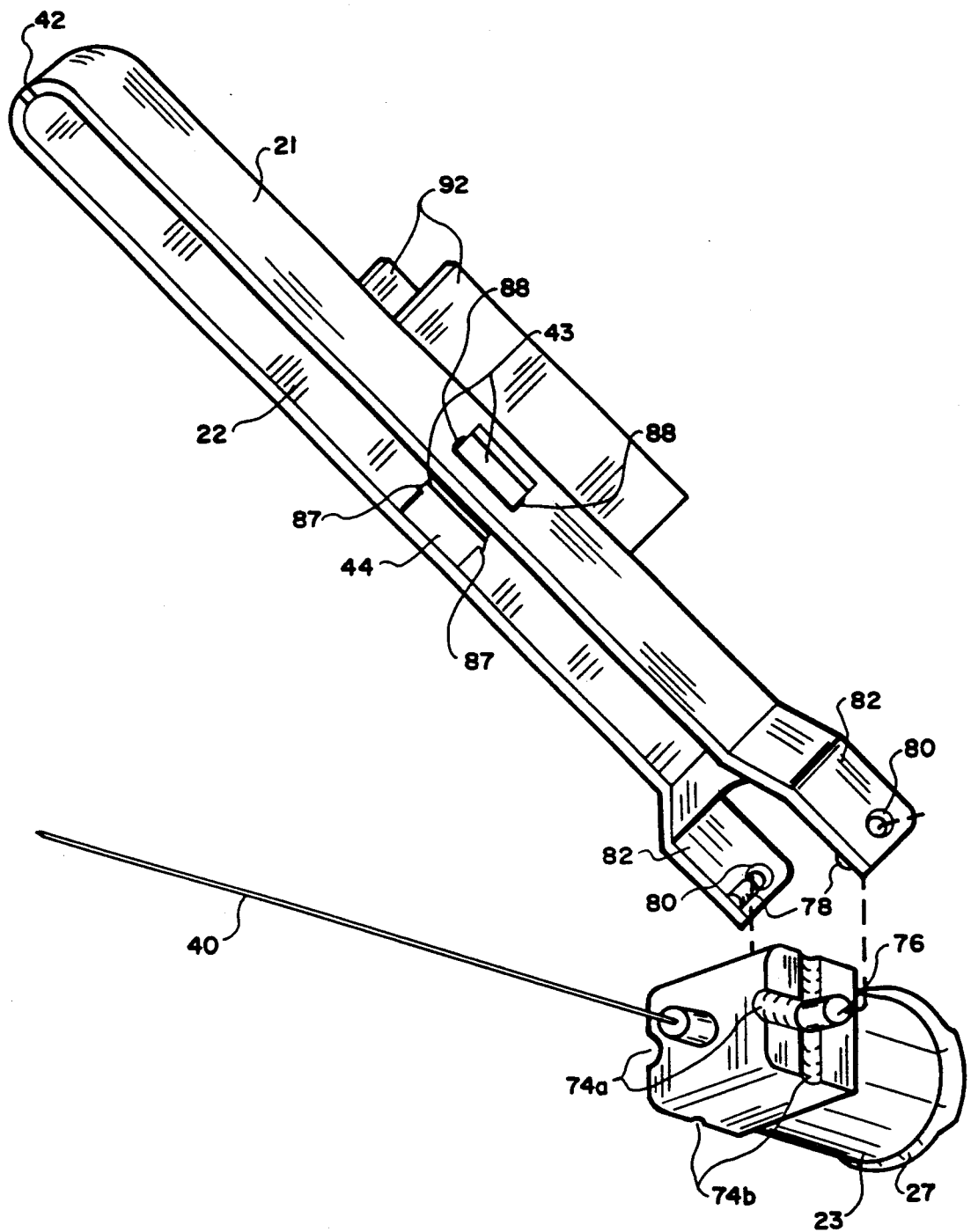
FIG. 23 is an axonometric, exploded view of the fourth embodiment of the invention, showing the addition of wing members.
Figure 24:
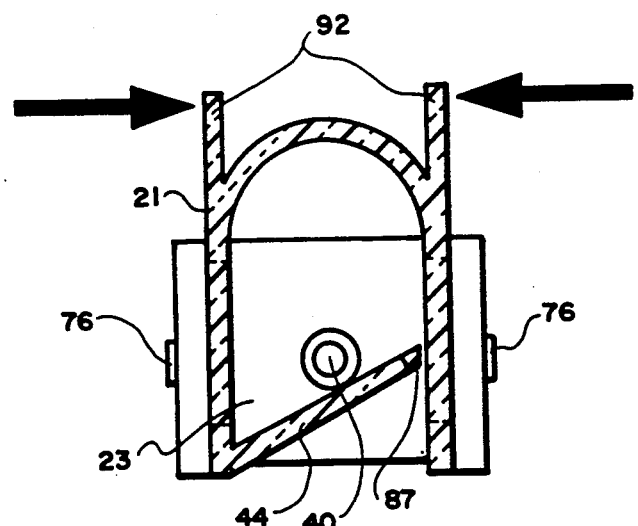
FIG. 24 is a section of the fourth embodiment of the invention to which wing members have been added, taken along the line H—H, and illustrating operation of the wing members.

The second variation involves addition of a set of wing members 92, as shown in FIGS. 23 and 24. By pinching the wing members together as shown in FIG. 24, the shape of longitudinal member 21 is distorted, widening the slot 22 and thereby increasing the distance between keeper shelf 44 and the side wall of longitudinal member 21 opposite keeper shelf 44. This allows for more convenient removal of the sheath, although it is still a two-handed operation.

The second embodiment of the invention is shown in FIGS. 9 through 15. Refer first to FIG. 7, which illustrates the basic structural features. As shown therein, needle hub 23 extends into spring arm 50, which depends from hub 23 as a sheath that is generally arcuate in cross-section. Spring arm 50 naturally assumes an angular position away from needle 40, thereby allowing the user to observe unimpeded the position of needle 40.

Spring arm 50 ultimately forms an elbow curl 52 and extends back toward the collar, thereby forming a lower arcuate portion 54 that acts as a trough for needle 40. Trough 54 terminates in a set of flanges 56 that further define the trough.

The user sheaths needle 40 by flexing spring arm 50 toward and to either side of needle 40 until trough 54 passes therebeneath. The user then moves spring arm 50 laterally so that needle 20 enters the space between spring arm 50 and trough 54. When the user releases spring arm 50, it naturally bends upward and thereby urging needle 40 against trough 54 so that the assembly assumes the position depicted in FIG. 10.

Figure 11:
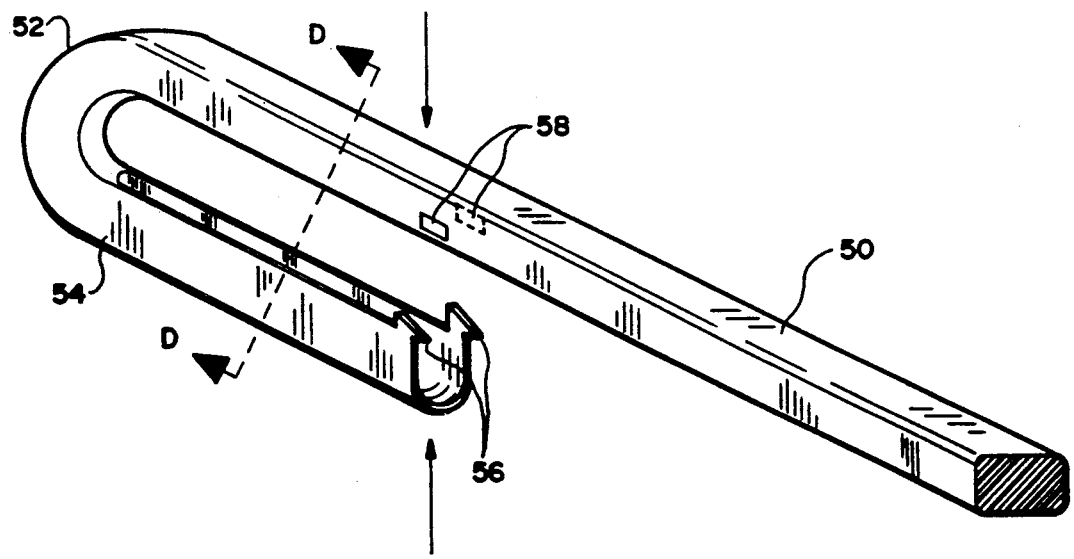
FIG. 11 is an axonometric view of the operative portion of the second embodiment of the invention.

This embodiment may also be provided with a locking mechanism, as shown in FIG. 11. This mechanism can consist, for example, of shaped flanges 56 that fit within a set of complementary detents 58 in spring arm 50.

Figure 12:
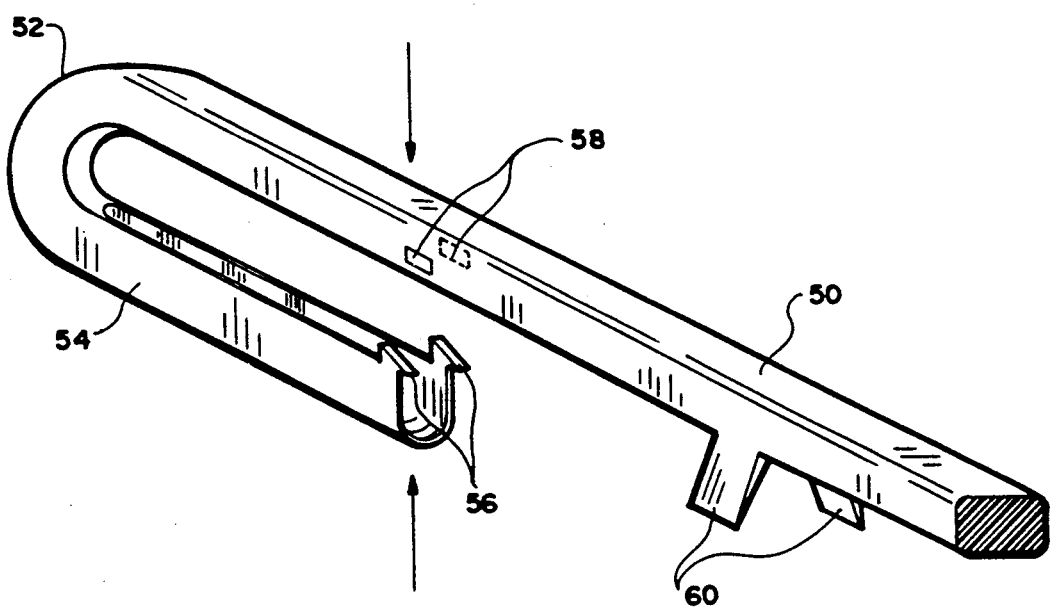
FIG. 12 shows the device illustrated in FIG. 11, which has been equipped with alignment flanges.
Figure 13:
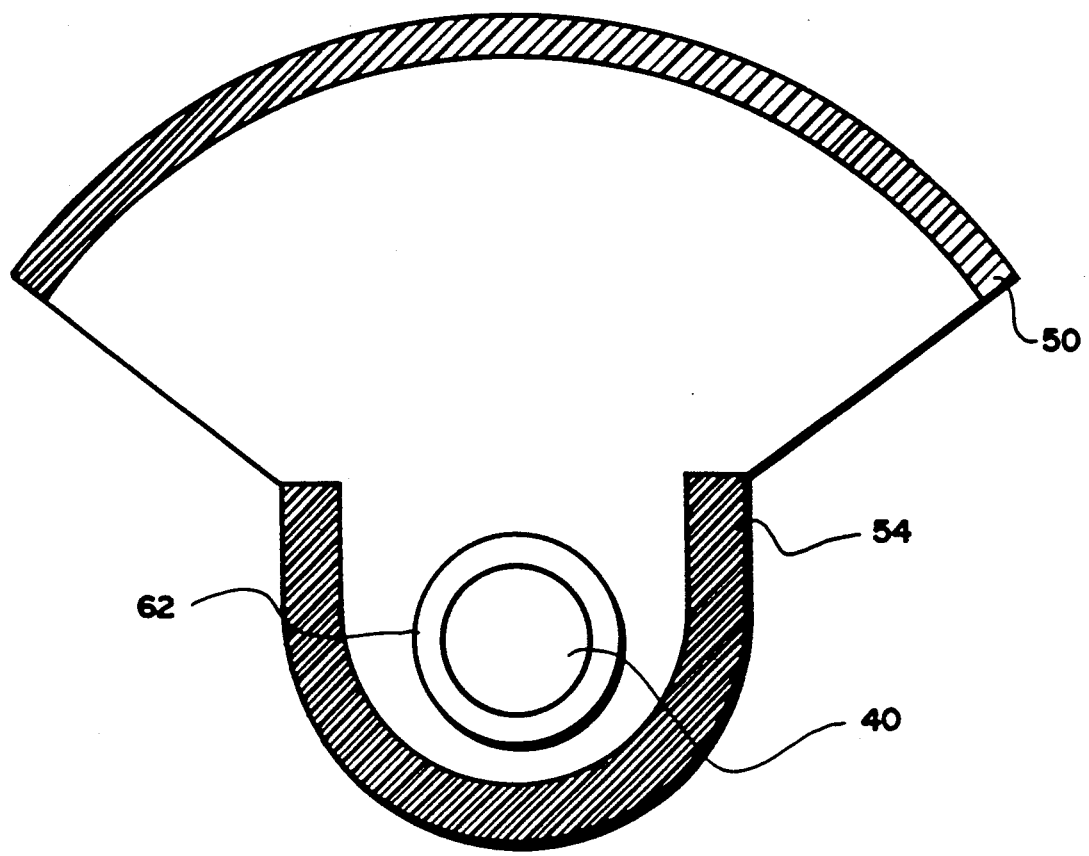
FIG. 13 is a section taken along line D—D of FIG. 11.

Two additional, optional design features may be added to promote accurate alignment of the device with needle 40. As shown in FIG. 12, two wing flanges 60 protrude outwardly from spring arm 50. As the user bends spring arm 50 downward to sheath needle 40, wing flanges 60 will catch needle 40 if it deviates from alignment with spring arm 50, and restore such alignment as the user continues to exert force. A second optional feature is shown in FIG. 13, which is a sectional view along line D—D of FIG. 11. As illustrated therein, the arcuate curvature of spring arm 50 can be broader than that of trough 54. In addition to facilitating alignment, the greater arcuate dimension of spring arm 50 reduces the chances of accidental contact with needle 40.

Also depicted in FIG. 13 is a hole 62, which permits ejection of fluid through needle 40 while the sheath remains in the closed position.

Figure 14:
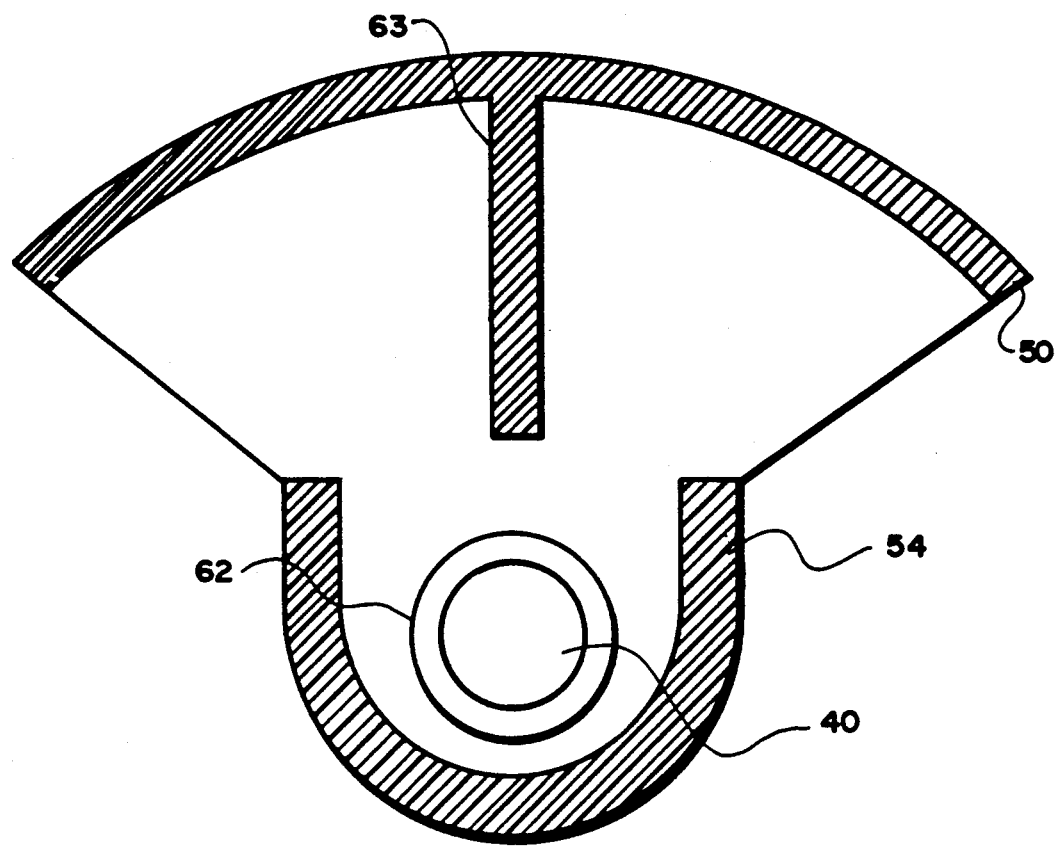
FIG. 14 is a section of a variation of the second embodiment, taken along the line D—D of FIG. 11.

A variation of this embodiment is illustrated in FIG. 14. In this design, a vertical wall 63 depends downward from spring arm 50 and extends below the arcuate edges thereof. When the user moves spring arm 50 laterally in order to engage needle 40 within trough 54, vertical wall 63 acts as a stop to block lateral movement of needle 40 beyond the well of trough 54. This feature adds an additional measure of safety by guiding the needle to its proper rest site.

Figure 15:
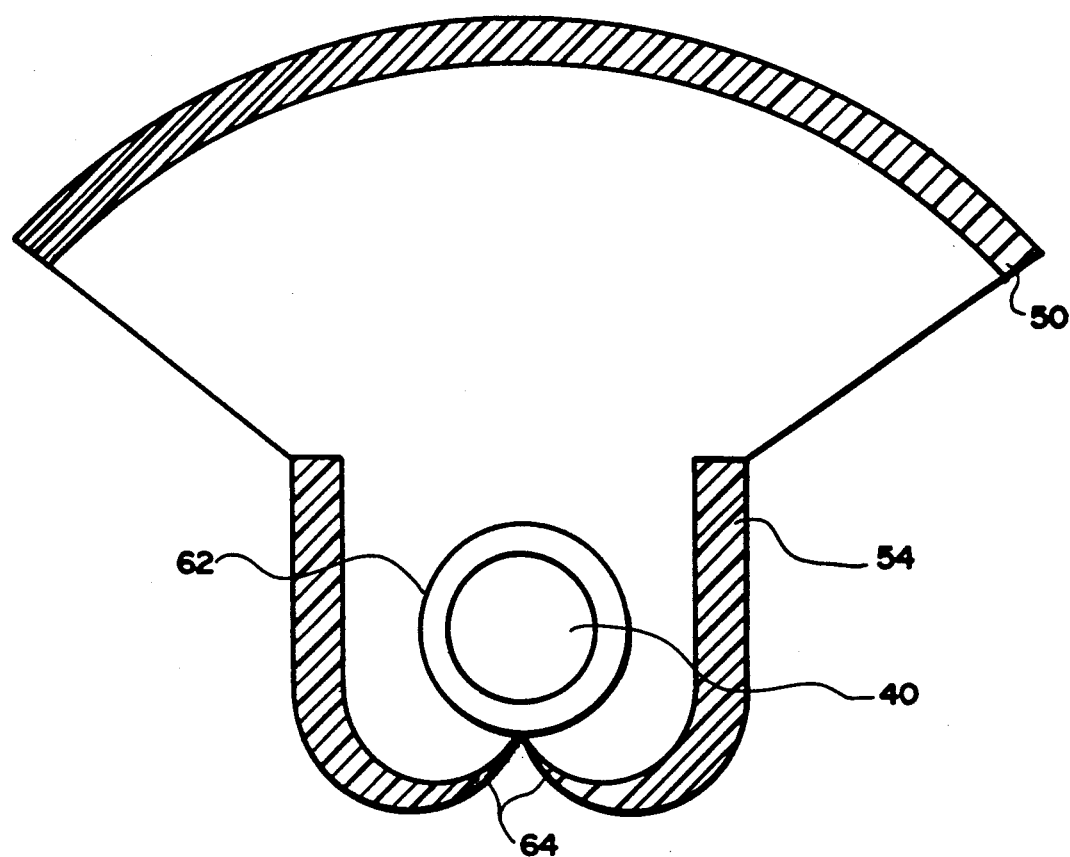
FIG. 15 is a section of the third embodiment of the invention, taken along line D—D of a modified version of the device depicted in FIG. 11.
Figure 16:
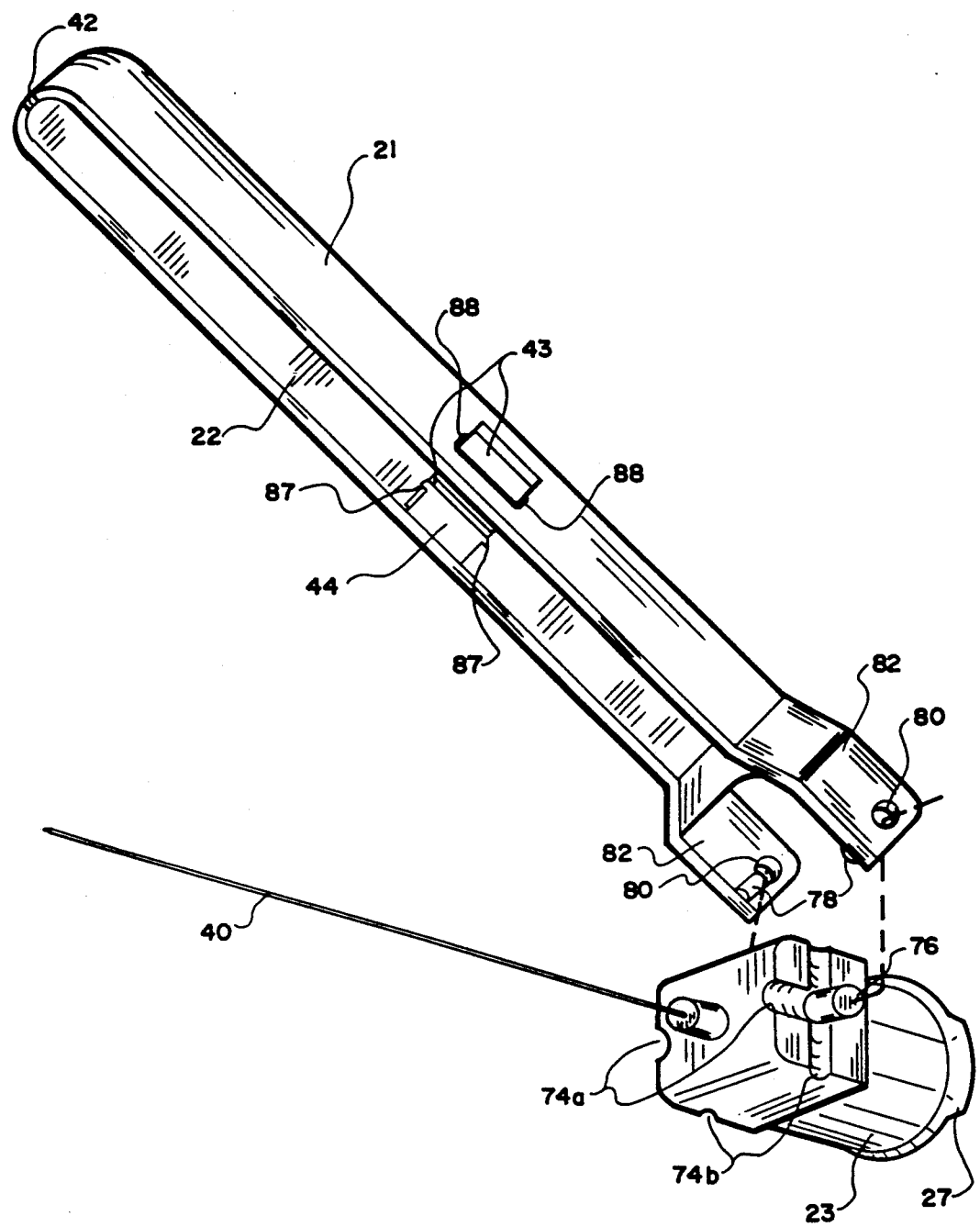
FIG. 16 is an axonometric, exploded view of the fourth embodiment of the invention.
Figure 17:
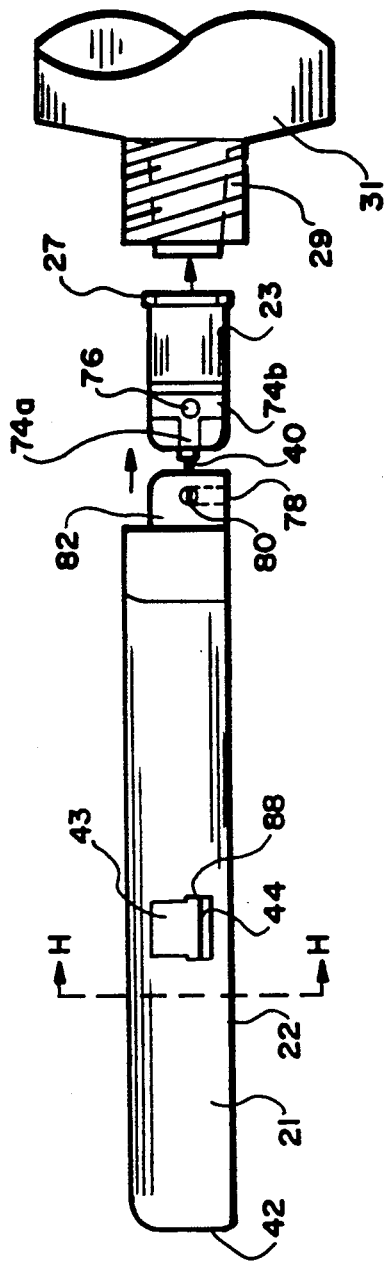
FIG. 17 is a side elevational view of the device depicted in FIG. 16.
Figure 18:
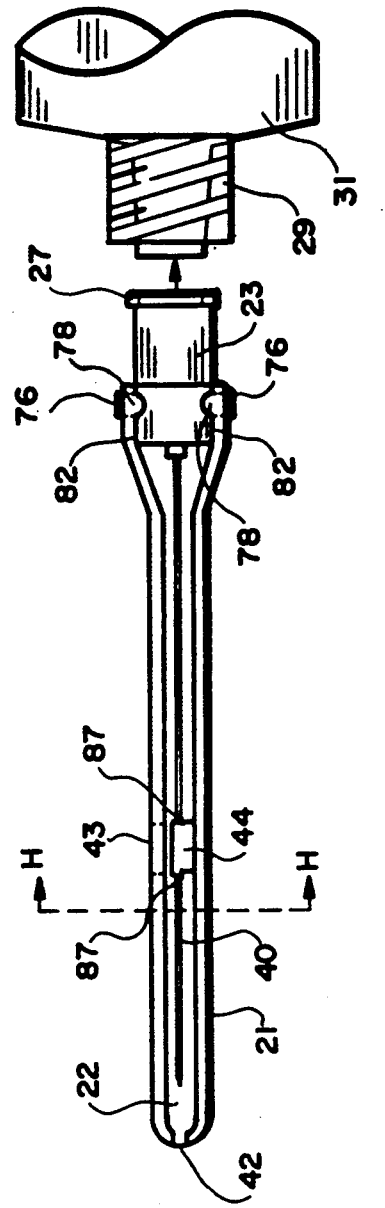
FIG. 18 is a bottom view of the device depicted in FIG. 16.
Figure 19:
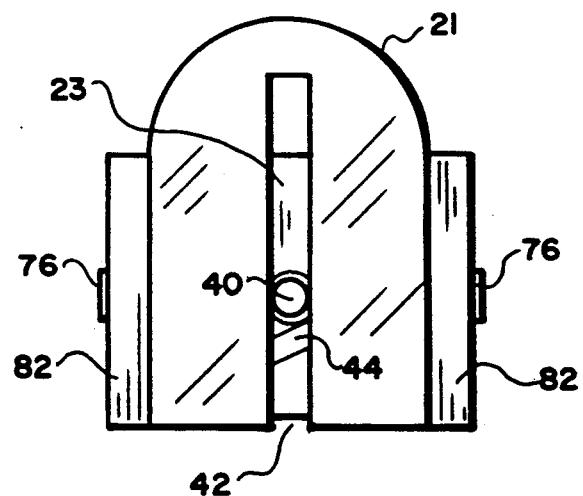
FIG. 19 is a frontal view of the device depicted in FIGS. 16-18, labeled as "View G" in FIGS. 17 and 18.
Figure 20:
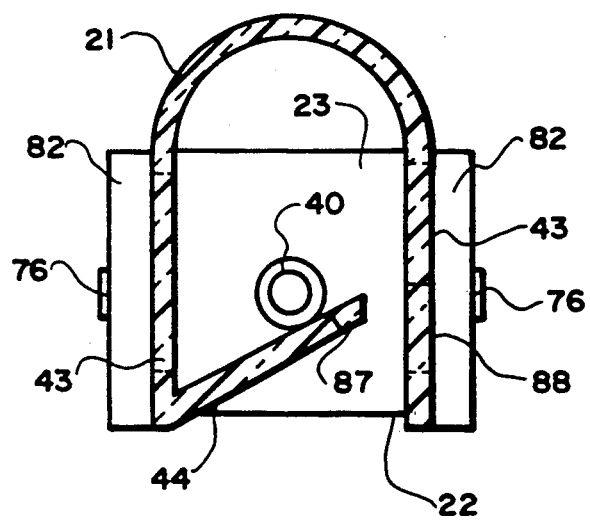
FIG. 20 is a section of the fourth embodiment of the invention, taken along the line H—H of FIGS. 17 and 18.

The third embodiment is illustrated in FIG. 15. In this embodiment, trough 54 is replaced with two soft, upwardly curved flanges 64. These flanges form a trapping arrangement, which captures needle 40 as it is driven therebetween by the user's flexion of spring arm 50. Although the upward curve of flanges 64 permits needle 40 to be guided past flanges 64 with a minimum of applied force, the same is not true of movement in the opposite direction, which will actually be opposed by the curvature of flanges 64. This embodiment may also be equipped with wing flanges 60 and/or wall 63.

Figure 21:
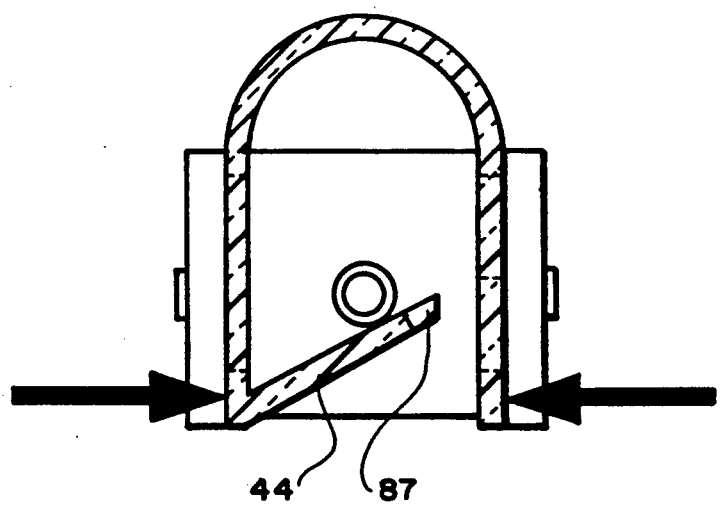
FIGS. 21 and 22 are sectional views along the line H—H that illustrate operation of the sheath locking mechanism.
Figure 22:
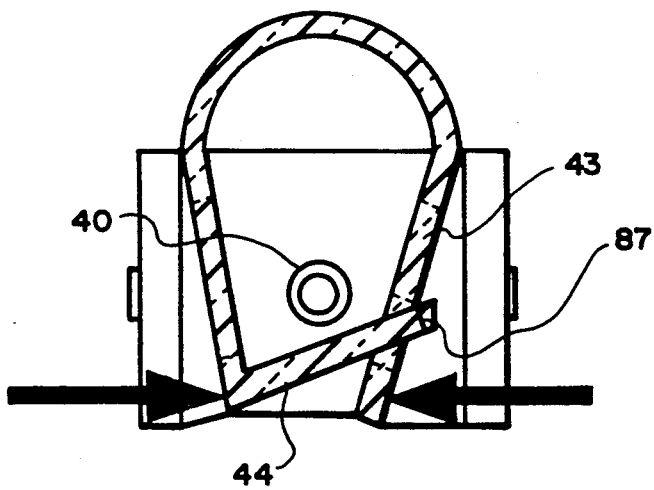

The fourth embodiment is illustrated in FIGS. 16 through 24. This variation is structurally similar to the first embodiment, but contains a sheath locking mechanism and the position-holding feature described above. This mechanism consists of a set of barbs 87 on the free edge of keeper shelf 44. By laterally pinching longitudinal member 21 as shown in FIGS. 21 and 22, these barbs are forced through window 43 on the opposite side of longitudinal member 21. Barbs 87 are shaped to catch the outer surface of longitudinal member 21 so as to prevent movement of the shelf back through the window. Barbs 87 can be shaped to produce a desired degree of locking permanence. Furthermore, the lower section 88 of window 43 can be widened to encourage penetration of barbs 87 therethrough, rather than allowing them to slide up unnecessarily along the inside of window 43 before penetration.

Figure 25:
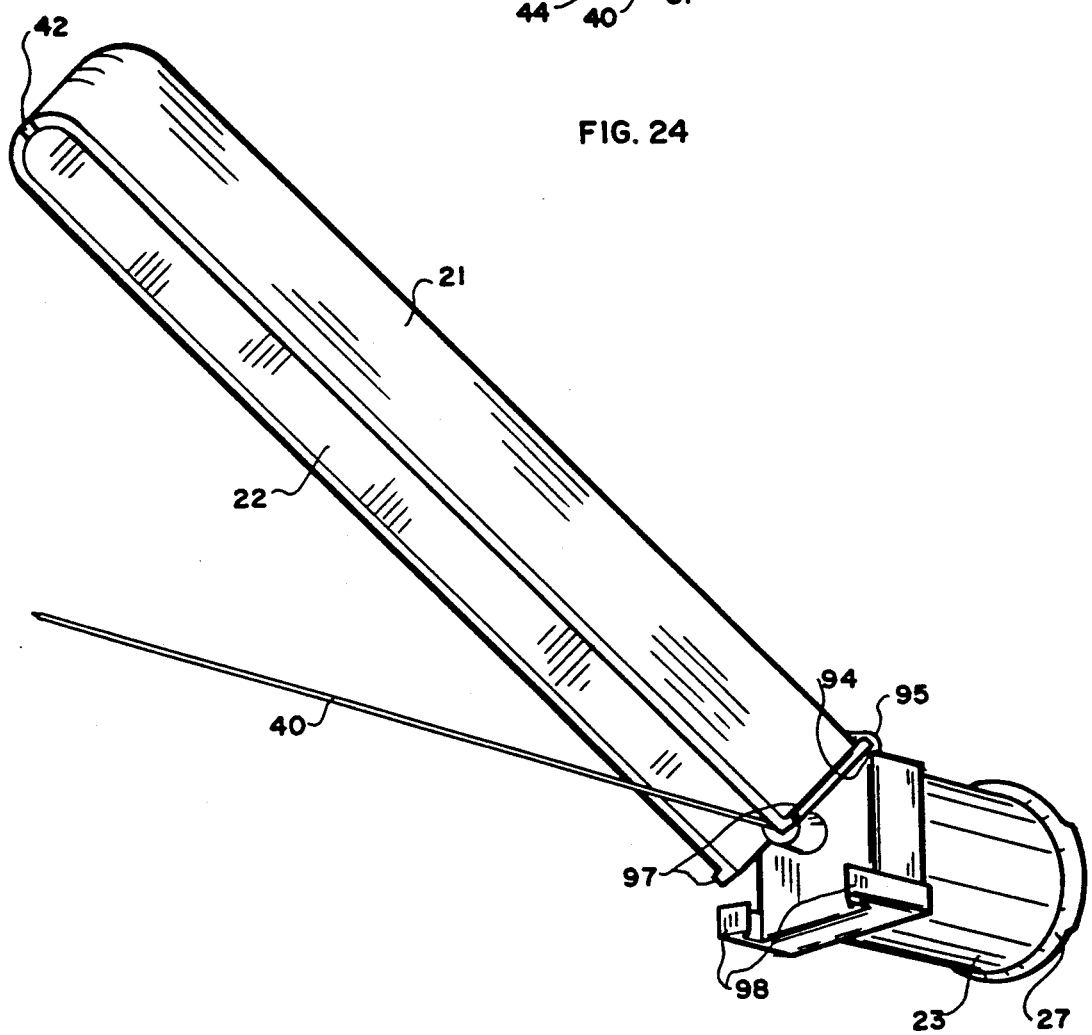
FIG. 25 is an axonometric view of the fifth embodiment of the invention in the open (rest) position.
Figure 26:
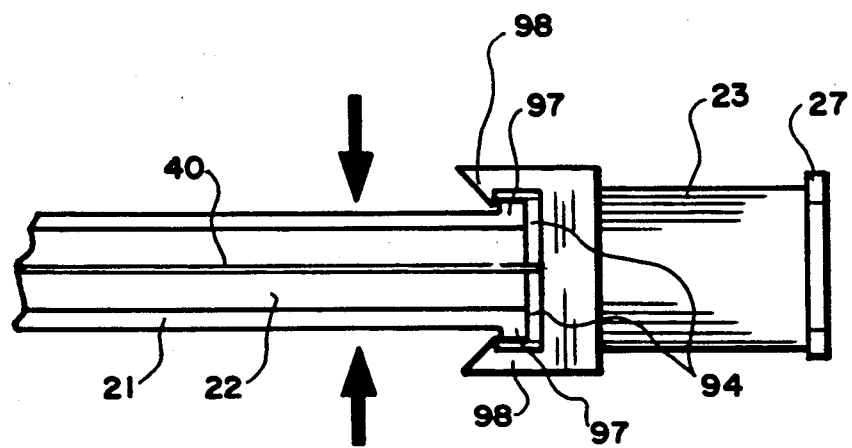
FIG. 26 is a bottom view of the device depicted in FIG. 25, illustrating use of the locking mechanism and the axis of force applied to pinch it open.
Figure 27:
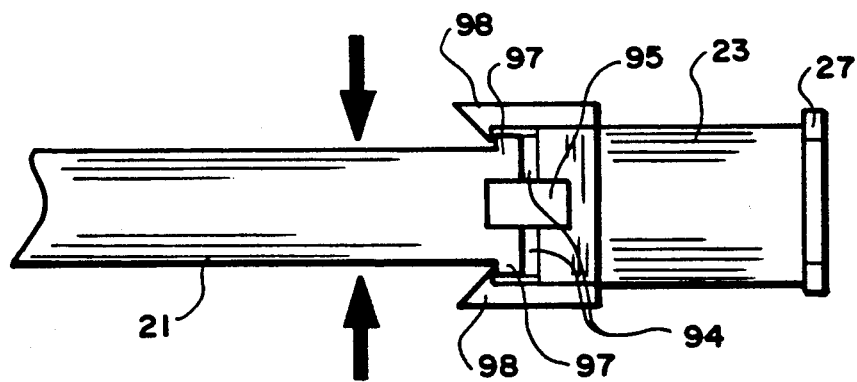
FIG. 27 is a top plan view of the device depicted in FIG. 25, illustrating use of the locking mechanism and the axis of force applied to pinch it open.

The fifth embodiment is shown in FIGS. 25-29. In this one-piece version, the keeper-shelf locking mechanism is replaced with a set of flanges and complimentary catches. This is illustrated in FIG. 25. Two integral catches 98 depend from needle hub 23, and engage a complimentary set of flanges 97 that protrude outwardly from the base of longitudinal member 21. The operation of the locking mechanism is shown in FIG. 26. When longitudinal member 21 is placed into the closed position, flanges 97 snap past catches 98 to fit within the space behind them. The action of the locking mechanism can be reversed, and longitudinal member 21 opened to expose needle 40, by pinching the sides of longitudinal member 21 inwardly so as to compress flanges 97 within the space separating catches 98. The catches can be gripped by the user when the device is twisted onto a syringe or intravenous tube, either in addition or as an alternative to the torque vanes shown in FIG. 2.

Figure 28:
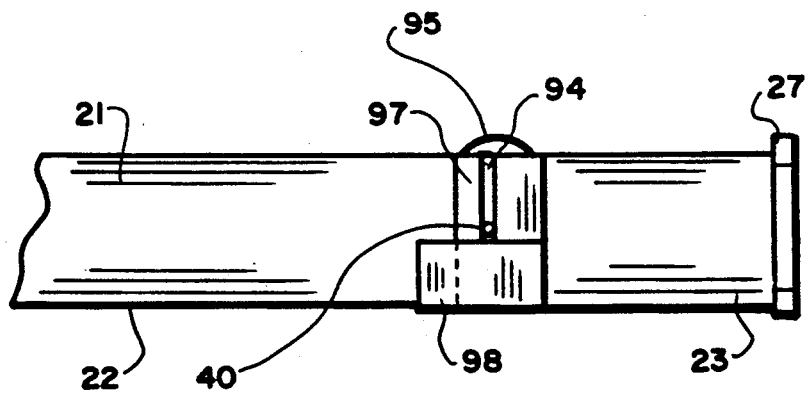
FIG. 28 is a side elevational detail of the fifth embodiment in the closed (taut) position.
Figure 29:
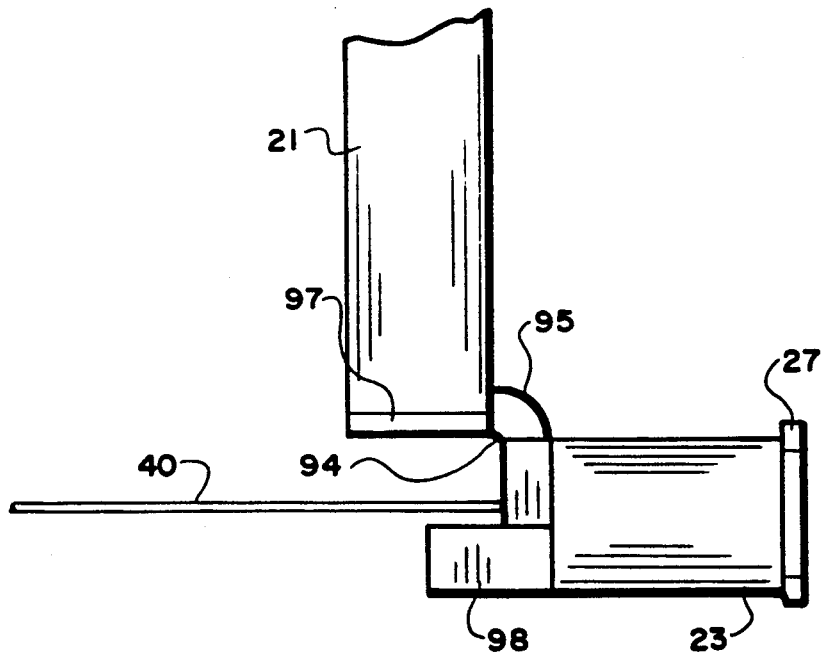
FIG. 29 is a side elevational detail of the fifth embodiment in the open (rest) position.

Preferably, this embodiment is provided with a hinge means that retains longitudinal member 21 in the open position unless positively locked by the user. A suitable arrangement is depicted most clearly in FIGS. 27-29. Longitudinal member 21 is attached to needle hub 23 by means of a living hinge 94 and a strap spring 95. Spring 95 is molded to be at rest when longitudinal member 21 forms a desired angle with respect to needle hub 23 (preferably 90 degrees), and resists further movement of longitudinal member 23 toward the user; this is illustrated in FIG. 29. In FIG. 28, with the device in the closed position, spring 95 is taut.

Variations on this design are possible. For example, the catches can depend from longitudinal member 21 and engage a flange protruding from needle hub 23. This design requires application of outward (rather than inward) force to disengage the locking mechanism; such force can be applied, for example, by means of wing flanges mounted on longitudinal member 21 as shown in FIG. 23. Alternative spring designs are also possible.

This version of the invention is readily molded in one piece by injection, and retains the advantage of requiring a two-handed operation for opening. It is well-suited for use with thin or delicate tools or needles, since the locking mechanism operates independently thereof and cannot cause structural damage thereto.

The terms and expressions which have been employed are used as terms of description and not of limitation, and there is no intention, in the use of such terms and expressions, of excluding any equivalents of the features shown and described or portions thereof, but it is recognized that various modifications are possible within the scope of the invention claimed. For example, the various hinges illustrated for the sheath-type embodiments can be interchanged to accommodate manufacturing or ease-of-use considerations.

What is claimed is:

1. A safety sheath assembly for use with a surgical instrument having a sharp end, the assembly comprising:
    a. a collar disposed on the instrument in advance of the sharp end;
    b. a sheath integral with the collar, having an anterior portion hingedly affixed to the collar, and having a posterior portion with an axial slot wider than the sharp end of the instrument,
wherein
    c. the posterior portion of the sheath fixedly but removably engages the collar or the instrument upon closure of the sheath over instrument by means of flanges on the sheath that fit within complementary catches on the collar or instrument;
    d. the posterior portion of the sheath disengages the collar or instrument upon application thereto of a pinching force and is thereafter urged to an open position with respect to the instrument; and
    e. the posterior portion of the sheath extends beyond the sharp end of the instrument.

2. The assembly of claim 1 further comprising means for urging the sheath to a predetermined position with respect to the instrument.

3. A safety sheath assembly for use with a needle mounted in a hub, the assembly comprising a sheath integral with the hub, the sheath having an anterior portion hingedly affixed to the hub and a posterior portion with an axial slot, wherein:
    a. the anterior portion of the sheath fixedly but removably engages the hub upon closure of the sheath over the needle by means of flanges on the sheath that fit within complementary catches on the hub;
    b. the anterior portion of the sheath disengages the hub upon application thereto of a pinching force and is thereafter urged to an open position with respect to the hub; and
    c. the posterior portion of the sheath extends beyond the needle.

* * * * *